United States Patent [19]

Tobe et al.

[11] Patent Number: 5,434,665
[45] Date of Patent: Jul. 18, 1995

[54] ATOMIC ABSORPTION ANALYZING APPARATUS WITH ADJUSTABLE CARRIER GAS FLOW RATE

[75] Inventors: Hayato Tobe; Katsuhito Harada, both of Katsuta, Japan

[73] Assignee: Hitachi, Ltd., Tokyo, Japan

[21] Appl. No.: 101,870

[22] Filed: Aug. 4, 1993

[30] Foreign Application Priority Data

Aug. 5, 1992 [JP] Japan ................... 4-208343

[51] Int. Cl.$^6$ ............................ G01N 21/74
[52] U.S. Cl. ........................ 356/307; 356/312
[58] Field of Search ............... 356/307, 311, 312

[56] References Cited

U.S. PATENT DOCUMENTS

| | | | |
|---|---|---|---|
| 3,811,778 | 5/1974 | Hadeishi | 356/312 |
| 4,314,764 | 2/1982 | Liddell et al. | 356/315 |
| 5,104,220 | 4/1992 | Okumoto et al. | 356/307 |

FOREIGN PATENT DOCUMENTS 5144833 12/1976 Japan .
2259450 10/1990 Japan .

OTHER PUBLICATIONS

"HGA-500 Graphite Furnace", Perkin-Elmer brochure, Aug. 1978, p. 5.

*Primary Examiner*—Vincent P. McGraw
*Attorney, Agent, or Firm*—Kenyon & Kenyon

[57] ABSTRACT

A sample disposed in a graphite tube in a furnace is subjected to thermal treatment at successive stages, drying, ashing and atomization and atomic absorption due to an element contained in the sample is measured. Amounts of inert carrier gas supplied to the graphite tube are different for different samples. The carrier gas flow rate at each of the stages is varied so as to reduce influences of background when each of the samples is treated. The carrier gas flow rate is varied, depending on the magnitude of a background signal measured on the basis of light which has passed through the graphite tube.

10 Claims, 3 Drawing Sheets

ATOMIC ABSORPTION ANALYZING APPARATUS WITH ADJUSTABLE CARRIER GAS FLOW RATE

BACKGROUND OF THE INVENTION

The present invention relates to an atomic absorption analyzing apparatus, and in particular to an atomic absorption analyzing apparatus, which is so constructed that inert gas is supplied to a graphite tube.

Two types of sample atomizing means for an atomic absorption spectrophotometer are known. One of them is a type, by which a flame is formed over a burner and the other is a type, by which a graphite furnace is used. The present invention relates to the latter.

U.S. Pat. No. 5,104,220 teaches temperature control means for giving the graphite furnace a drying stage, an ashing stage and an atomization stage. This prior art further splitting atomic absorption lines of an element to be examined by the Zeeman effect by applying a magnetic field to the graphite furnace.

In the atomic absorption spectrophotometer using a graphite furnace, generally inert gas is supplied to the graphite tube, to prevent thermal damage to the graphite tube. JP-B-51-44833 discloses varying a flow rate of inert gas supplied to the graphite tube as carrier gas, depending on the processing stage for the sample. That is, this prior art teaches to control the carrier gas flow rate so that it is smaller at the atomization stage than at the ashing stage. Owing thereto, atomic vapor of a metal element stays as long as possible in the graphite furnace at the atomization stage and disturbing matter such as particles is rapidly exhausted from the graphite furnace at the ashing stage.

JP-A-2-259450 indicates to keep the graphite furnace at a drying temperature for 60 sec., at an ashing temperature for 20 sec. and at an atomization temperature for 5 sec., and to set the flow rate of argon gas at two values, i.e., 5 ml/min. and 200 ml/min. It is set at 200 ml/min. for the drying stage and at 5 ml/min. for the atomization stage. This prior art teaches that it is set at 200 ml/min. for the first 15 sec. of the ashing stage and at 5 ml/min. for the last 5 sec. thereof.

These prior art techniques disclose setting the flow rate of carrier gas supplied to the graphite tube, depending on the stage, drying, ashing or atomization. However, according to these prior art techniques, the carrier gas flow rate, which has been once set for each of the stages, remains constant and is not varied, even if the sample is changed.

SUMMARY OF THE INVENTION

The present invention pays attention to the fact that the magnitude of background produced by heating of the furnace differs and the amount of carrier gas to be required varies, when the sample is changed.

The present invention supplies carrier gas at a suitable flow rate for every sample to be analyzed in order to increase signal to noise ratio.

The present invention also supplies carrier gas at a suitable flow rate at each of the different stages, drying, ashing and atomization.

An atomic absorption analyzing apparatus according to the present invention comprises means for supplying carrier gas of inert gas to a sample heating tube such as a graphite tube disposed in a furnace, means for heating the sample heating tube so as to produce drying, ashing and atomization for a sample located in the sample heating tube, means for measuring a magnitude of background, based on light which has been transmitted by the sample heating tube, at each of a drying stage, an ashing stage and an atomization stage, and flow rate control means for controlling flow rate of a carrier gas to be supplied to the sample heating tube for each stage, depending on the magnitude of background in each of the different stages described above.

The flow rate control means maintains the carrier gas at a predetermined flow rate at the initiation of each of the drying stage, the ashing stage and the atomization stage.

A signal coming from the measuring means described above at each stage is compared with a set value and judging means judges, on the basis of a comparison result thus obtained, if the carrier gas flow rate should be maintained or increased. This judging means judges whether the carrier gas flow rate should be reduced to zero or not at the atomization stage for the sample.

The flow rate control means controls the flow rate on the basis of a judgment result obtained by the judging means. For the carrier gas flow rate to be applied, this flow rate control means selects one of a plurality of carrier gas flow rates previously determined stepwise.

At the atomization stage for the sample, the judging means judges how great a suitable carrier gas flow rate should be, also taking into account a condition concerning the magnitude of atomic absorption due to an element to be examined, when absorbance (R) due to background is smaller than 1.5. For example, the judging means judges it suitable to increase the carrier gas flow rate, when the absorbance due to the atomic absorption described above is greater than 0.2 and to reduce the carrier gas flow rate to zero, when the absorbance due to the atomic absorption described above is smaller than 0.01.

From another point of view, an analyzing apparatus according to the present invention comprises:
means for storing a plurality of classification regions of the magnitude of background for each of the drying stage, the ashing stage and the atomization stage;
means for judging to what classification region the magnitude of background measured at each of the stages corresponds; and
means for regulating the carrier gas flow rate so as to be in accordance with a stored carrier gas flow rate corresponding to a result obtained by the judging means.

The classification region storing means stores a plurality of classification regions of the magnitude of background and a plurality of classification regions of the magnitude of atomic absorption for the atomization stage and the judging means described above judges to what classification regions the magnitude of background and the magnitude of atomic absorption due to the element to be examined measured for the atomization stage correspond.

In the case where $R \leq 1.5$ at the drying stage and the ashing stage, since the background signal is not excessively great, the supplied amount of carrier gas is set at $(200 \pm 20)$ % of the volume of the sample tube per sec. so as to exhaust molecular or particle component, while in the case where $R > 1.5$, since the background signal is excessively great, the supplied amount of carrier gas is increased to $(400 \pm 20)$ % so as to accelerate the exhaustion of molecular or particle component.

The exhaustion of molecular or particle component is continued also at the atomization stage by supplying carrier gas. However, since sample atoms are also exhausted at the same time as the exhaustion of molecular or particle component and intensity of the signal is decreased, the supplied amount of carrier gas is set at the optimum value, depending on the magnitude of the background and the signal.

That is, in the case where the background signal (absorbance ABS value) R at the atomization stage is smaller than 0.05, the supplied amount of carrier gas is reduced to zero for atomic absorption signal (absorbance ABS value) $S<0.01$. The supplied amount of carrier gas is set at $(65\pm20)$ % of the volume of the sample tube per sec. for $0.01\leqq S<0.2$ and at $(200\pm20)$ % of the volume of the sample tube per sec. for $0.2\leqq S$.

Further, in the case where $0.05\leqq R<1.5$, the supplied amount of carrier gas is set at $(65\pm20)$ % of the volume of the sample tube per sec. for $S\leqq0.2$ and at $(200\pm20)$ %/sec. for $0.2\leqq S$, and in the case where $R>1.5$, it is set at $(200\pm20)$ %/sec.

DETAILED DESCRIPTION

Figure 1:
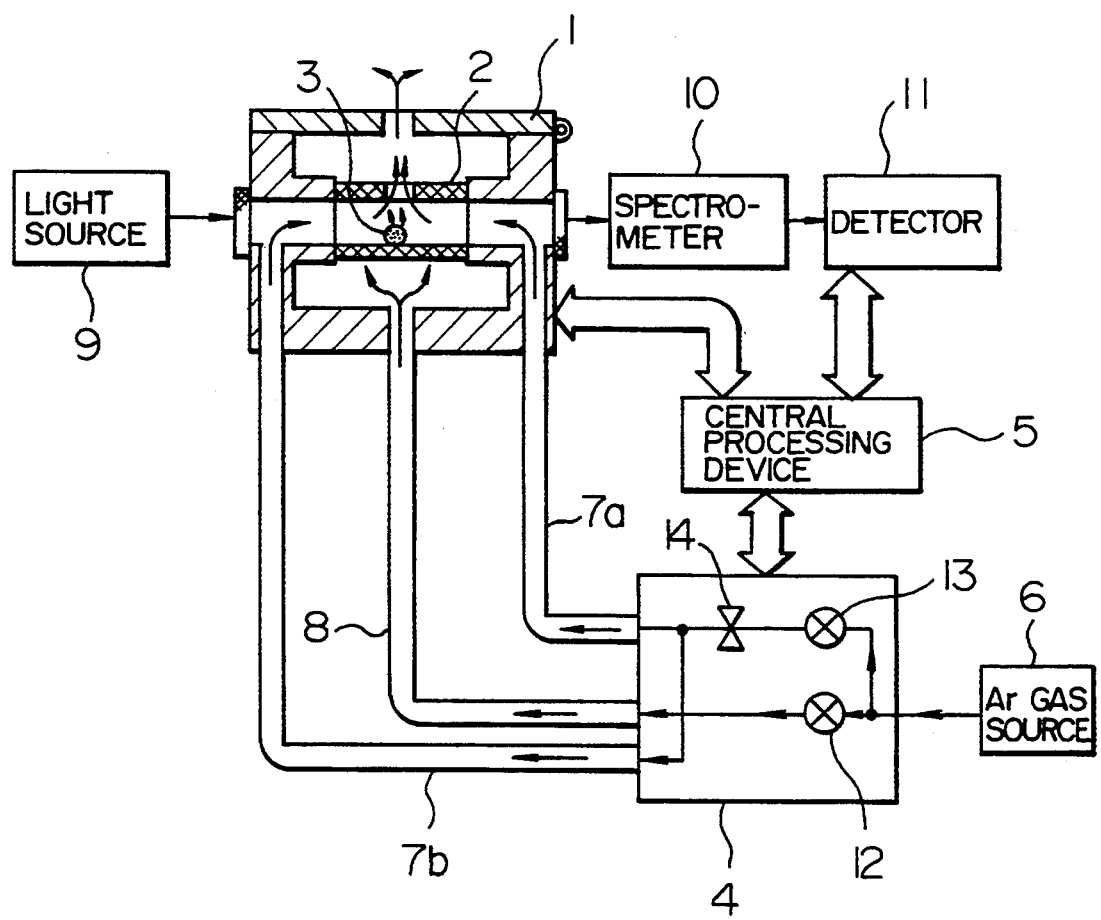
FIG. 1 is a schematic diagram representing the construction of an embodiment of the present invention.

In FIG. 1, a graphite tube 2 serving as a sample heating tube is heated successively stepwise at the drying stage, the ashing stage and the atomization stage. The graphite tube 2 is located in a furnace 1 and a sample 3 containing an element to be measured is introduced into the graphite tube 2 through a through-hole formed in an upper cover of the furnace 1 and a sample insertion hole formed in the tube 2.

The temperature of the graphite tube is raised by feeding the furnace 1 with electric power. The temperature of the graphite tube 2 is raised to 70° to 150° C. at the drying stage. The duration of the drying stage is 45 to 60 seconds. The temperature of the graphite tube 2 is raised to 200° to 1000° C. at the ashing stage. The duration of the ashing stage is 20 to 30 seconds. The temperature of the graphite tube 2 is raised to 1500° to 2900° C. at the atomization stage. The duration of the atomization stage is 4 to 5 seconds.

A central processing device 5 has not only an operational function but also a function to compare the magnitude of background measured on the basis of light transmitted by the graphite tube 2 with a value previously set and to judge on the basis of a comparison result thus obtained how the carrier gas flow rate should be varied. Further the central processing device 5 is provided with a memory for storing a plurality of classification regions of the magnitude of background at each of the stages and flow rates of carrier gas to be supplied corresponding to these classification regions, respectively.

A gas control section 4 controls the amount of carrier gas to be supplied to the heating furnace 1. Ar gas, which is an inert gas, is supplied from a gas source 6 to the interior of the graphite tube 2 through a two-way electromagnetic valve 13, a flow rate regulator 14 and carrier gas pipes 7a and 7b and to the exterior of the graphite tube 2 through a two-way electromagnetic valve 12 and a sheath gas pipe 8.

Oxidation of the heating furnace 1 and thermal damage of the graphite tube 2 are prevented by supplying Ar gas from the gas source 6 to the interior and the exterior of the graphite tube 2. At the same time the supplied gas exhausts at measurement disturbing matter such as molecules, particles, etc. produced within the graphite tube 2 to the outside of the graphite tube 2 to reduce a background component in the atomic absorption.

The central processing device 5 controls both temperature as well as duration thereof for the heating furnace 1 and flow rate changing operation of the gas control section 4.

A light beam emitted by a light source 9 is partly absorbed by molecules and particles within the graphite tube 2 as well as vapor of atoms of the sample and injected into a spectrometer 10.

Some of monochromatic light dispersed by the spectrometer 10 is detected by a photodetector 11 having a plurality of detection areas.

When the graphite tube 2 is heated, disturbing matters such as microparticles, smoke, etc. is produced from the sample 3. These disturbing matters decrease the intensity of the light beam passing through the graphite tube 2. The produced amount of disturbing matters varies with time. Therefore production of the disturbing matters absorbs specified wavelengths for the atomic absorption by the element to be examined and wavelengths other than the specified wavelengths. Measured data on the light which has passed through the graphite tube 2 are converted generally into absorbance to be dealt with.

The furnace 1 is located in a gap between magnetic poles of an electromagnet. Since the monochromatic beam emitted from a hollow cathode lamp serving as the light source 9 is subjected to the Zeeman effect by the magnetic field, the polarized component parallel to the magnetic field remains as analysis wavelength, while the polarized component perpendicular to the magnetic field is split to wavelengths distant from the analysis wavelength. Since these polarized components are separated into their spectral components by the spectrometer 10, the parallel polarized component is detected by a photodetector 11 as light absorbed by the atomic vapor of the element to be examined. The perpendicular polarized component is detected by the photodetector 11 in order to measure the background due to the disturbing matters within the graphite tube 2.

The detection of the background due to the disturbing matters can be achieved also by atomic absorption spectrophotometers using no magnet. In such a case a two wavelengths measuring method may be adopted.

The central processing device 5 deals with an absorbance signal due to the background obtained by the detector 11 and an absorbance signal due to the atomic absorption produced by the atomic vapor of the element to be examined to calculate the absorbance only due to the element to be examined in the sample.

The background signal R is measured at the drying stage and the ashing stage to be compared with a reference value and the supplied amount of carrier gas is corrected, depending on a result thus obtained. At the atomization stage both the background signal R and the atomic absorption signal S are measured and the supplied amount of carrier gas is corrected, depending on a combination thereof.

At the drying stage carrier gas is supplied to the graphite tube 2 at an initial flow rate of 100 ml/min. At the same time the graphite tube 2 is heated to 70° C. and thereafter to 150° C. At the ashing stage carrier gas is supplied to the graphite tube 2 at an initial flow rate of 100 ml/min. At the same time the graphite tube 2 is heated to 200° C. and thereafter to 1000° C. Finally at the atomization stage carrier gas is supplied to the graphite tube 2 at an initial flow rate of 30 ml/min. At the same time the graphite tube 2 is heated to 2700° C.

Next the background signal (absorbance ABS) R is detected by the detector 11 to be compared with the predetermined reference value by the central processing device 5 and the supplied amount of carrier gas is corrected, if necessary.

Figure 2:
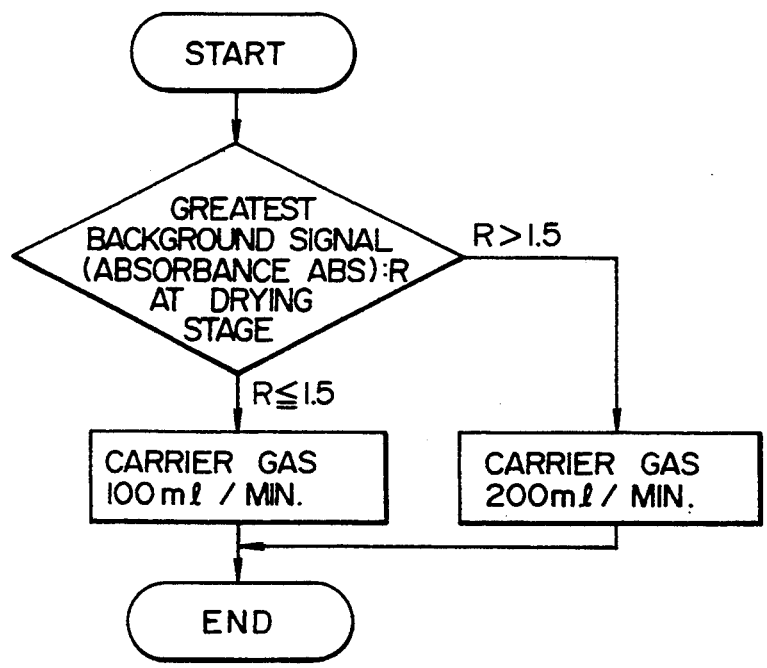
FIG. 2 is a flow chart for setting the carrier gas flow rate at the drying stage.

FIG. 2 is a flow chart for determining the optimum supplied amount of carrier gas at the drying stage.

If the background signal (absorbance ABS) R is smaller than 1.5, since it can be judged that molecules and particles causing the background signal R are exhausted satisfactorily, the supplied amount of carrier gas is set at a value in a region of $(200 \pm 20)$ %/sec. of the volume of the graphite tube 2. 100 ml/min. in the present embodiment is an example of the value in the region described above in the case where the inner volume of the graphite tube 2 is 0.82 $cm^3$. Carrier gas may be supplied over the region but in this case carrier gas is consumed in vain.

On the contrary, in the case where $R > 1.5$, since exhaustion of the molecules and particles described above is unsufficient, the supplied amount of carrier gas is increased to a value in a region of $(400 \pm 20)$ %/sec. of the volume of the graphite tube 2, that is, to 200 ml/min.

In FIG. 2 the magnitude of R has been judged by using 1.5 as a borderline. However it is possible also to optimize R more precisely by storing a relation representing variations of the optimum supplied amount of carrier gas with respect to R in the form of a table in the central processing device 5 and by reading out the optimum supplied amount of carrier gas in the table, depending on R.

Next the central processing device 5 sends commands to the heating furnace 1 and the flow rate regulator 14. The heating furnace 1 heats the graphite tube 2 to a specified ashing temperature and the flow rate regulator 14 sets the flow rate at 100 ml/min. The background signal R is detected in the same way to be compared with a reference value and the supplied amount of carrier gas is corrected, if necessary.

Figure 3:
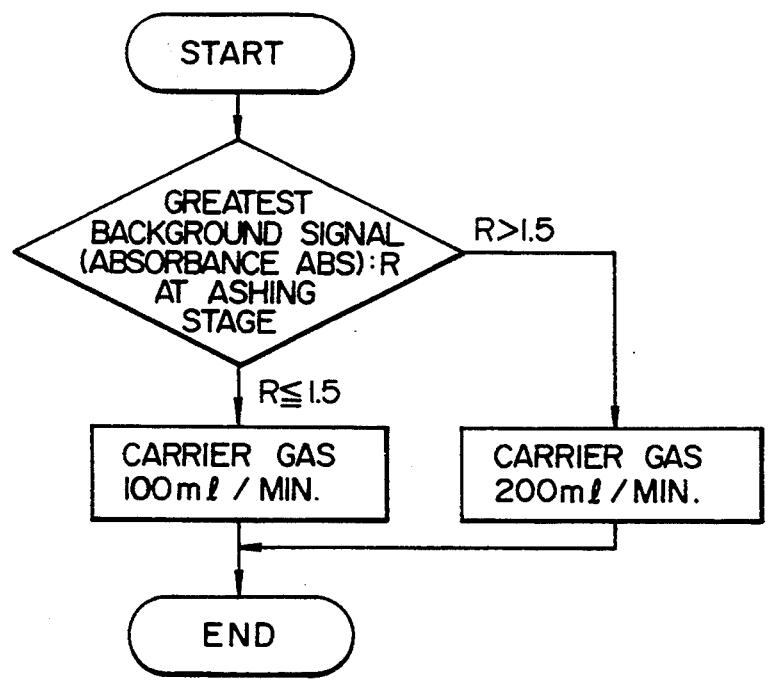
FIG. 3 is a flow chart for setting the carrier gas flow rate at the ashing stage.

FIG. 3 is a flow chart for determining the optimum supplied amount of carrier gas at the ashing stage. Although FIG. 3 is similar to FIG. 2, since the quantity of molecules and particles causing the background signal R varies, when the temperature of the graphite tube 2 is changed from drying to ashing, the procedure indicated in FIG. 3 is effected again.

At this time the optimum supplied amount of carrier gas with respect to R may be read out from the table in the central processing device 5.

Volatilization of the molecules and particles causing the background component can be accelerated by setting appropriately the optimum supplied amount of carrier gas at the dry stage and the ashing stage to exhaust them and it is possible also to reduce consumption of Ar gas.

Next the temperature of the graphite tube 2 is changed to atomization and at the same time the supplied amount of carrier gas supplied to the interior of the graphite tube 2 is set at a value in the region of $(65 \pm 20)$ %/sec. of the volume of the graphite tube 2, i.e. 30 ml/min.

Figure 4:
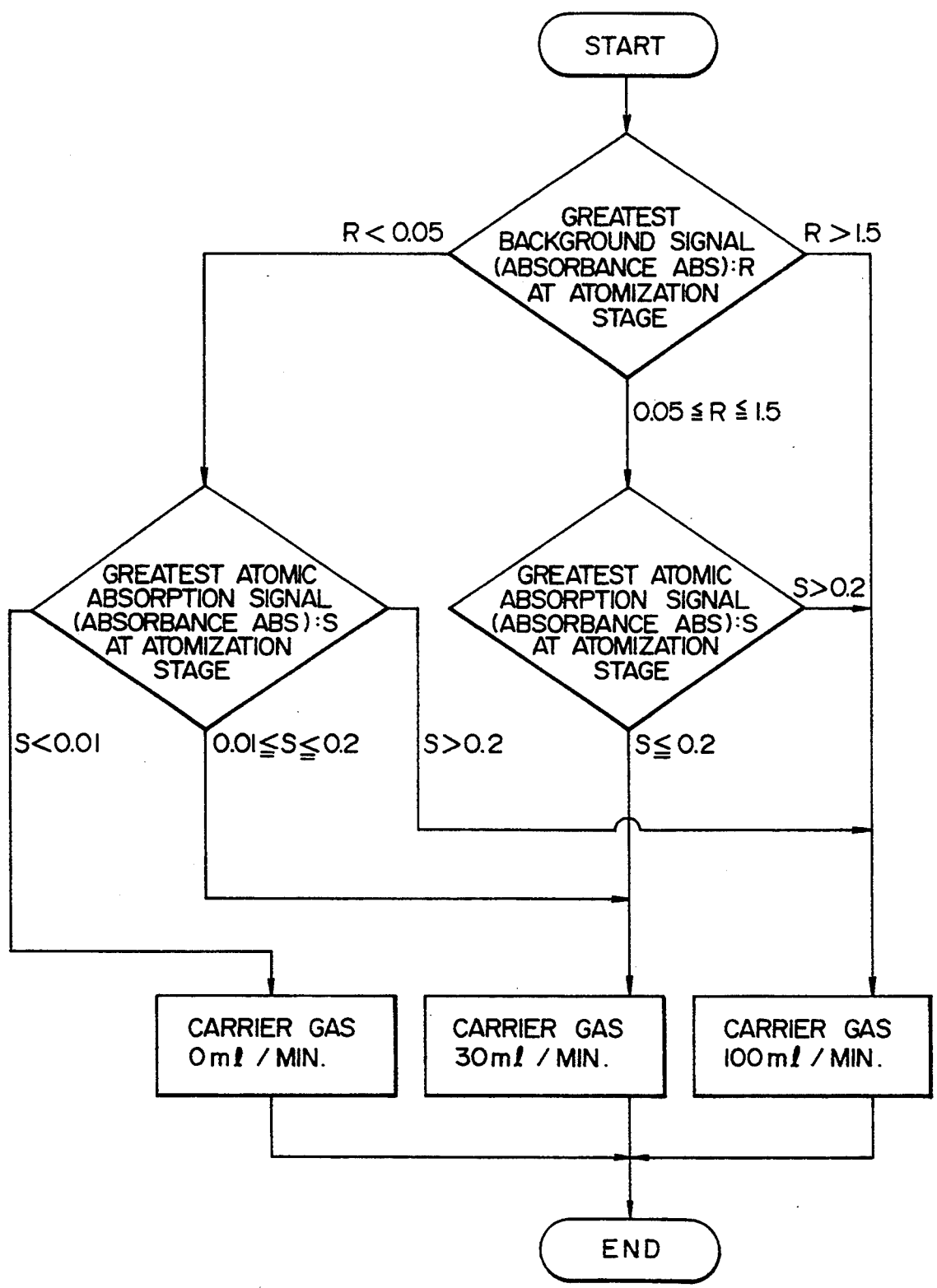
FIG. 4 is a flow chart for setting the carrier gas flow rate at the atomization stage.

FIG. 4 is a flow chart for determining the optimum supplied amount of carrier gas at the atomization stage. At the atomization stage the magnitude of the background R is classified into $R < 0.05$, $0.05 \leq R < 1.5$ and $1.5 < R$. Further for every classification region of R the atomic absorption signal (absorbance ABS) S is measured and classified and the supplied amount of carrier gas is determined, corresponding to each of the classification regions. In the case where $1.5 < R$, since R is too great, the supplied amount of carrier gas is set at 100 ml/min. similarly to the cases indicated in FIGS. 2 and 3.

In the case where $R < 0.05$, if $S < 0.01$, since it is judged that the number of atoms of the sample is extremely small, supply of carrier gas is stopped (0 ml/min. ) to prevent exhaustion of atoms of the sample.

If $0.01 < S < 0.2$, since S is sufficiently great for $R < 0.05$, the supplied amount of carrier gas is left at 30 ml/min. which is the reference value.

In the case where $0.2 < S$, the supplied amount of carrier gas is increased to 100 ml/min. to optimize the number of atoms of the sample.

When $0.05 \leq R < 1.5$, if $0.01 \leq S < 0.2$, since the magnitude of S is appropriate, the supplied amount of carrier gas is left at 30 ml/min. which is the reference value.

Further, although the supplied amount of carrier gas was determined by the relationship of R and S in the magnitude in FIG. 4, the relation of variations of the supplied amount of carrier gas with respect to R and S may be stored, e.g., in the form of a table in the central processing device 5 so as to be able to read out the supplied amount of carrier gas from the table described above, depending on the values of R and S.

After having set the supplied amount of carrier gas as described above, the atomic absorption signal S is converted into absorbance or concentration of the sample to obtain a measurement result and to terminate the measurement.

What is claimed is:

1. An atomic absorption analyzing apparatus comprising:
    a heater heating a sample heating tube so as to produce drying, ashing and atomization for a sample located in said sample heating tube;
    a gas supply supplying a carrier gas of inert gas at a respective predetermined initial flow rate for the start of each of said drying, ashing and atomization stages;
    background detector detecting magnitude of background, based on light which has passed through said sample heating tube at said atomization stage; and
    flow rate controller controlling flow rate of carrier gas to be supplied to said sample heating tube, depending on the magnitude of background detected by said background detector.

2. An atomic absorption analyzing apparatus according to claim 1, further comprising a comparator comparing a signal coming from said background detector at an initial period in the atomization stage with a set value and a processor judging if the carrier gas flow rate should be maintained or increased or reduced to zero, based on a result obtained from said comparator, said flow rate controller controlling the flow rate, based on a judgment result obtained by said processor.

3. An atomic absorption analyzing apparatus according to claim 2, wherein said flow rate controller selects one of a plurality of carrier gas flow rates previously determined step wise for the carrier gas flow rate to be applied.

4. An atomic absorption analyzing apparatus according to claim 2, wherein said processor judges the appropriate carrier gas flow rate taking into account a magnitude of atomic absorption due to an element to be examined, when absorbance due to background is detected to be smaller than 1.5.

5. An atomic absorption analyzing apparatus according to claim 4, wherein said processor determines it suitable to increase the carrier gas flow rate, when the absorbance due to said atomic absorption is greater than 0.2 and to reduce the carrier gas flow rate to zero, when the absorbance due to said atomic absorption is smaller than 0.01.

6. An atomic absorption analyzing apparatus comprising:
a heater heating a sample heating tube so as to produce drying, ashing and atomization for a sample located in said sample heating tube;
a gas supply supplying a carrier gas of inert gas at a respective predetermined initial flow rate for a start of each of said drying, ashing and atomization stages;
background detector detecting magnitude of background, based on light which has been transmitted by said sample heating tube at each of said drying stage, said ashing stage and said atomization stage; and
flow rate controller controlling a flow rate of carrier gas to be supplied to said sample heating tube, for each of said drying, ashing and atomization stages, depending on the magnitude of background thus obtained.

7. An atomic absorption analyzing apparatus according to claim 6, wherein said flow rate controller means for maintaining carrier gas at a predetermined flow rate at an initiation of each of said drying stage and said ashing stage and said apparatus further comprises a comparator comparing a signal coming from said detector at each initial period in the drying an ashing stages with a set value and judging if the carrier gas flow rate should be maintained or increased, based on a comparison result thus obtained.

8. An atomic absorption analyzing apparatus comprising:
a heater heating a sample heating tube so as to produce drying, ashing and atomization for a sample located in said sample heating tube;
a gas supply supplying a carrier gas of inert gas at a respective predetermined initial flow rate for a start of each of said drying ashing and atomization stages;
storage device storing a plurality of classification regions of the magnitude of background at said ashing stage;
means for judging the magnitude of background measured at the ashing stage for the sample;
a storage device storing a value identifying an amount of carrier gas corresponding to each of said plurality of classification regions; and
a controller controlling flow rate of said carrier gas so as to be in accordance with a stored said value identifying an amount of carrier gas corresponding to a result obtained by said means for judging.

9. An atomic absorption analyzing apparatus according to claim 8, wherein said stored value identifies an amount of carrier gas of $(200\pm20)$ %/sec of an inner volume of said sample heating tube per sec. and $(400\pm20)$ %/sec.

10. An atomic absorption analyzing apparatus according to claim 8, wherein said storing device storing said classification regions stores a plurality of classification regions of magnitude of background and a plurality of classification regions of atomic absorption at the atomization stage and said means for judging judges whether a magnitude of background measured at the atomization stage and a magnitude of atomic absorption due to the element to be examined correspond to relevant classification regions or not.

* * * * *

UNITED STATES PATENT AND TRADEMARK OFFICE
CERTIFICATE OF CORRECTION

PATENT NO. : 5,434,665

DATED : July 18, 1995

INVENTOR(S) : Hayato TOBE et al.

It is certified that error appears in the above-identified patent and that said Letters Patent is hereby corrected as shown below:

| Column | Line | |
|---|---|---|
| 1 | 19 | After "further" insert --indicates--. |
| 1 | 61 | Change "stages, drying" to --stages of drying--. |
| 2 | 14 | After "and" insert --a--. |
| 2 | 58 | After "examined" insert --,--. |
| 2 | 59 | After "stage" insert --,--. |
| 3 | 25 | After "invention" change "," to --.--. |
| 3 | 27 | After "stage" change "," to --.--. |
| 3 | 29 | Change "stage, and" to --stage.--. |
| 4 | 24-25 | Change "matters" to --matter--. |
| 4 | 26 | Change "These" to --This--; change "matters decrease" to --matter decreases--. |

UNITED STATES PATENT AND TRADEMARK OFFICE
CERTIFICATE OF CORRECTION

PATENT NO. : 5,434,665
DATED : July 18, 1995
INVENTOR(S) : Hayato TOBE et al.

It is certified that error appears in the above-identified patent and that said Letters Patent is hereby corrected as shown below:

| Column | Line | |
|---|---|---|
| 4 | 29 | After "The" delete "produced". |
| 4 | 30 | Change "matters" to --matter produced--. |
| 4 | 31 | Change "matters" to --matter--. |
| 4 | 52 | Change "matters" to --matter--. |
| 4 | 54 | Change "matters" to --matter--. |
| 4 | 61 | After "examined" change "to calculate" to --, and calculates--; after "absorbance" insert --due--. |
| 4 | 62 | Delete "due". |
| 5 | 34 | Change "unsufficient" to --insufficient--. |
| 5 | 66 | Change "dry" to --drying--. |

UNITED STATES PATENT AND TRADEMARK OFFICE
CERTIFICATE OF CORRECTION

PATENT NO. : 5,434,665
DATED : July 18, 1995
INVENTOR(S) : Hayato TOBE et al.

It is certified that error appears in the above-identified patent and that said Letters Patent is hereby corrected as shown below:

| Column | Line | |
|---|---|---|
| 6 | 11 | After "Further" insert --,--. |
| 8 | 1 | Change "comprises" to --comprising--. |
| 8 | 3 | Change "an" to --and--. |
| 8 | 14 | After "drying" inert --,--. |
| 8 | 16 | Before "storage" insert --a--. |

Signed and Sealed this

Fourteenth Day of May, 1996

Attest:

BRUCE LEHMAN

*Attesting Officer*        *Commissioner of Patents and Trademarks*